United States Patent
Pearson et al.

(10) Patent No.: US 12,168,077 B2
(45) Date of Patent: Dec. 17, 2024

(54) ENERGY HARVESTING DUAL PURPOSE MONITORING TEMPERATURE AS A PHM SENSOR

(71) Applicant: GOODRICH CORPORATION, Charlotte, NC (US)

(72) Inventors: Matthew Robert Pearson, Hartford, CT (US); Eric Johannessen, Holbrook, NY (US)

(73) Assignee: GOODRICH CORPORATION, Charlotte, NC (US)

( * ) Notice: Subject to any disclaimer, the term of this patent is extended or adjusted under 35 U.S.C. 154(b) by 874 days.

(21) Appl. No.: 17/334,042

(22) Filed: May 28, 2021

(65) Prior Publication Data
US 2022/0378958 A1 Dec. 1, 2022

(51) Int. Cl.
| | |
|---|---|
| A61L 2/10 | (2006.01) |
| A61L 9/20 | (2006.01) |
| B64D 11/02 | (2006.01) |
| F21V 23/02 | (2006.01) |
| G21H 1/00 | (2006.01) |
| H05B 47/19 | (2020.01) |
| H05B 47/28 | (2020.01) |

(52) U.S. Cl.
CPC .............. *A61L 2/10* (2013.01); *A61L 9/20* (2013.01); *F21V 23/02* (2013.01); *G21H 1/00* (2013.01); *H05B 47/19* (2020.01); *H05B 47/28* (2020.01); *A61L 2202/11* (2013.01); *A61L 2202/25* (2013.01); *A61L 2209/12* (2013.01); *B64D 11/02* (2013.01)

(58) Field of Classification Search
CPC .......... A61L 2/10; A61L 9/20; A61L 2202/11; A61L 2202/25; A61L 2209/12; H05B 47/19; H05B 47/28; F21V 23/02; G21H 1/00; B64D 11/02
See application file for complete search history.

(56) References Cited

U.S. PATENT DOCUMENTS

| | | | |
|---|---|---|---|
| 6,107,756 | A | 8/2000 | Parra |
| 6,274,988 | B1 | 8/2001 | De Vries |
| 6,716,375 | B1 | 4/2004 | Powers et al. |
| 7,009,347 | B2 | 3/2006 | Henze |
| 10,418,233 | B2 | 9/2019 | Larson et al. |
| 2015/0194817 | A1 | 7/2015 | Lee et al. |
| 2018/0281241 | A1 | 10/2018 | Schropp et al. |
| 2021/0052757 | A1 | 2/2021 | Baarman |

FOREIGN PATENT DOCUMENTS

EP 3421053 1/2019

OTHER PUBLICATIONS

European Patent Office, European Search Report dated Sep. 20, 2022 in Application No. 22175774.3.

*Primary Examiner* — Nicole M Ippolito
*Assistant Examiner* — Hanway Chang
(74) *Attorney, Agent, or Firm* — SNELL & WILMER L.L.P.

(57) ABSTRACT

A system for monitoring an excimer bulb includes a thermoelectric energy harvester configured to be located adjacent to the excimer bulb and to convert thermal energy from the excimer bulb into electrical energy having a voltage. The system further includes a controller in electrical communication with the thermoelectric energy harvester and configured to calculate at least one of a remaining useful life of the excimer bulb or a current temperature of the excimer bulb based on the voltage of the electrical energy converted by the thermoelectric energy harvester.

20 Claims, 4 Drawing Sheets

ENERGY HARVESTING DUAL PURPOSE MONITORING TEMPERATURE AS A PHM SENSOR

FIELD

The present disclosure relates to systems and methods for monitoring an excimer bulb and, in particular, a system for monitoring an ultraviolet-emitting excimer bulb using an energy harvesting monitoring device.

BACKGROUND

Ultraviolet (UV) light has been found to be an effective disinfectant. Of the various UV wavelengths, 222 nanometers (222 nm) has been found to be particularly promising (effective and relatively safe for humans in moderate doses). Currently, UV lights that emit light of this wavelength are only available as gas-discharge excimer bulbs. These bulbs have longevity challenges and relatively low efficiency (e.g., less than 50 percent efficient) so a significant amount of this energy is dissipated as thermal energy. The relatively short lifetime of these bulbs (e.g., in the hundreds of hours) means that they should be replaced relatively frequently. Due to power and weight demands on board aircraft, it is desirable to monitor the status of these excimer bulbs using as little power as possible.

Thus, there is a need in the art for systems and methods for low-power monitoring of these ultraviolet-emitting UV excimer bulbs.

SUMMARY

Disclosed herein is a system for monitoring an excimer bulb. The system includes a thermoelectric energy harvester configured to be located adjacent to the excimer bulb and to convert thermal energy from the excimer bulb into electrical energy having a voltage. The system further includes a controller in electrical communication with the thermoelectric energy harvester and configured to calculate at least one of a remaining useful life of the excimer bulb or a current temperature of the excimer bulb based on the voltage of the electrical energy converted by the thermoelectric energy harvester.

In any of the foregoing embodiments, the controller is further configured to calculate the remaining useful life of the excimer bulb based on at least one of the current temperature of the excimer bulb, a previously-calculated historical temperature of the excimer bulb, the current voltage of the electrical energy converted by the thermoelectric energy harvester, or a previous voltage of the electrical energy converted by the thermoelectric energy harvester.

Any of the foregoing embodiments may further include a memory configured to store historical data corresponding to at least one the previously-calculated historical temperature of the excimer bulb or the previous voltage of the electrical energy converted by the thermoelectric energy harvester, and the controller is further configured to calculate the remaining useful life of the excimer bulb by comparing at least one of the current temperature of the excimer bulb or the current voltage of the electrical energy converted by the thermoelectric energy harvester to the historical data.

Any of the foregoing embodiments may further include a wireless transmitter coupled to the controller and configured to transmit the at least one of the remaining useful life of the excimer bulb or the current temperature of the excimer bulb to a remote device.

In any of the foregoing embodiments, the wireless transmitter is configured to be powered using the electrical energy generated by the thermoelectric energy harvester.

Any of the foregoing embodiments may further include a housing configured to house the thermoelectric energy harvester, the controller, and the wireless transmitter.

In any of the foregoing embodiments, the controller is configured to be powered using the electrical energy generated by the thermoelectric energy harvester.

In any of the foregoing embodiments, the excimer bulb emits ultraviolet light for damaging or destroying pathogens, and the system is configured for use in an aircraft.

In any of the foregoing embodiments, the controller is configured to calculate both of the remaining useful life of the excimer bulb and the current temperature of the excimer bulb.

In any of the foregoing embodiments, the controller is configured to calculate the remaining useful life of the excimer bulb as hours of useful life remaining.

Also disclosed is a system for monitoring an excimer bulb. The system includes a thermoelectric energy harvester configured to be located adjacent to the excimer bulb and to convert heat from the excimer bulb into electrical energy having a voltage. The system further includes a controller in electrical communication with the thermoelectric energy harvester and configured to: calculate a current temperature of the excimer bulb based on the voltage of the electrical energy converted by the thermoelectric energy harvester, and calculate a remaining useful life of the excimer bulb based on at least one of the voltage of the electrical energy converted by the thermoelectric energy harvester or the current temperature of the excimer bulb.

Any of the foregoing embodiments may further include a wireless transmitter coupled to the controller and configured to transmit at least one of the remaining useful life of the excimer bulb or the current temperature of the excimer bulb to a remote device.

Also disclosed is a method for monitoring an excimer bulb. The method includes converting, by a thermoelectric energy harvester, thermal energy received from an adjacent excimer bulb into electrical energy having a voltage. The method further includes calculating, by a controller, at least one of a remaining useful life of the excimer bulb or a current temperature of the excimer bulb based on the voltage of the electrical energy converted by the thermoelectric energy harvester.

In any of the foregoing embodiments, calculating the remaining useful life of the excimer bulb is performed based on at least one of the current temperature of the excimer bulb, a previously-calculated historical temperature of the excimer bulb, the current voltage of the electrical energy converted by the thermoelectric energy harvester, or a previous voltage of the electrical energy converted by the thermoelectric energy harvester.

Any of the foregoing embodiments may further include storing, in a memory, historical data corresponding to at least one the previously-calculated historical temperature of the excimer bulb or the previous voltage of the electrical energy converted by the thermoelectric energy harvester, wherein calculating the remaining useful life of the excimer bulb is performed by comparing at least one of the current temperature of the excimer bulb or the current voltage of the electrical energy converted by the thermoelectric energy harvester to the historical data.

Any of the foregoing embodiments may further include transmitting, by a wireless transmitter, the at least one of the remaining useful life of the excimer bulb or the current temperature of the excimer bulb to a remote device.

In any of the foregoing embodiments, the wireless transmitter is powered using the electrical energy generated by the thermoelectric energy harvester.

In any of the foregoing embodiments, the controller is powered using the electrical energy generated by the thermoelectric energy harvester.

In any of the foregoing embodiments, calculating the at least one of the remaining useful life of the excimer bulb or the current temperature of the excimer bulb includes calculating both of the remaining useful life of the excimer bulb and the current temperature of the excimer bulb.

In any of the foregoing embodiments, calculating the remaining useful life of the excimer bulb includes calculating a number of hours of remaining useful life remaining.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the figures, wherein like numerals denote like elements.

DETAILED DESCRIPTION

The detailed description of exemplary embodiments herein makes reference to the accompanying drawings, which show exemplary embodiments by way of illustration. While these exemplary embodiments are described in sufficient detail to enable those skilled in the art to practice the exemplary embodiments of the disclosure, it should be understood that other embodiments may be realized and that logical changes and adaptations in design and construction may be made in accordance with this disclosure and the teachings herein. Thus, the detailed description herein is presented for purposes of illustration only and not limitation. The steps recited in any of the method or process descriptions may be executed in any order and are not necessarily limited to the order presented.

Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts but not necessarily to denote the same or different materials.

The present disclosure is directed to systems and methods for monitoring the status of an ultraviolet (UV)-emitting excimer bulb. The systems and methods may be implemented in an aircraft which has significant weight and power demands. Due to these demands, it is highly desirable to use as little power as possible to monitor the status of these bulbs. In that regard, the present disclosure presents a monitoring device that is self-powering using a thermal-to-electric (thermoelectric) energy harvester between the bulb and its thermal heat sink. The thermoelectric energy harvester powers a controller which may calculate a remaining useful life or a current temperature of the excimer bulb based on the voltage of the energy generated by the energy harvester, and a wireless transmitter that transmits the remaining useful life or the current temperature to an aircraft controller.

The ultraviolet excimer bulbs of the present disclosure may emit far UV-C light. This light may be defined as a germicidal light source having a peak wavelength that is between 200 nanometers (200 nm, 0.00787 thousandths of an inch, or mils) and 230 nm (0.00906 mils), between 210 nm (0.00827 mils) and 225 nm (0.00886 mils), or about 222 nm (0.00874 mils). Where used in this context, "about" refers to the referenced value plus or minus 10 percent of the referenced value.

UV light of this type may effectively injure, neutralize, or kill pathogens that are both airborne and resting on surfaces. In addition, this light may be readily absorbed by most materials and may be relatively safe for human exposure.

Figure 1:
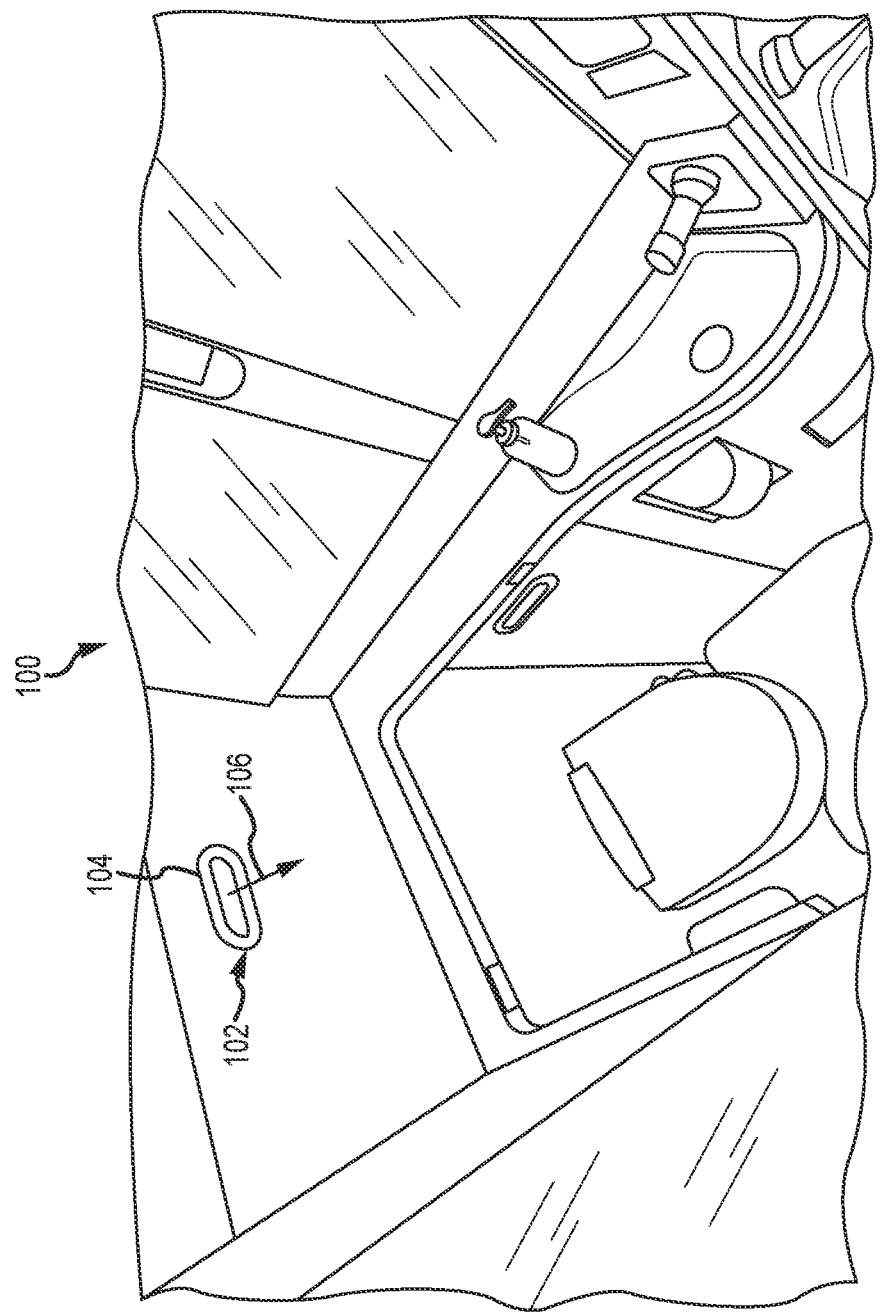
FIG. 1 illustrates an aircraft lavatory having an excimer ultraviolet bulb and a monitoring device capable of monitoring a status of the excimer ultraviolet bulb, in accordance with various embodiments.

Referring now to FIG. 1, a portion of an aircraft lavatory 100 may include one or more UV excimer bulb 102. The excimer bulb 102 may emit UV light towards a portion of the lavatory 100, as shown by an arrow 106. The lavatory 100 may further include a monitoring device 104.

Figure 2A:
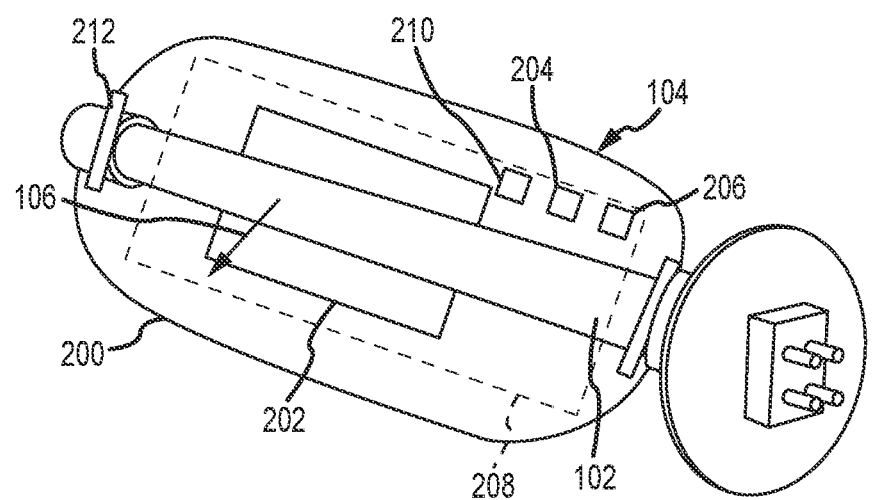
FIGS. 2A and 2B illustrate various features of the monitoring device of FIG. 1, in accordance with various embodiments.
Figure 2B:
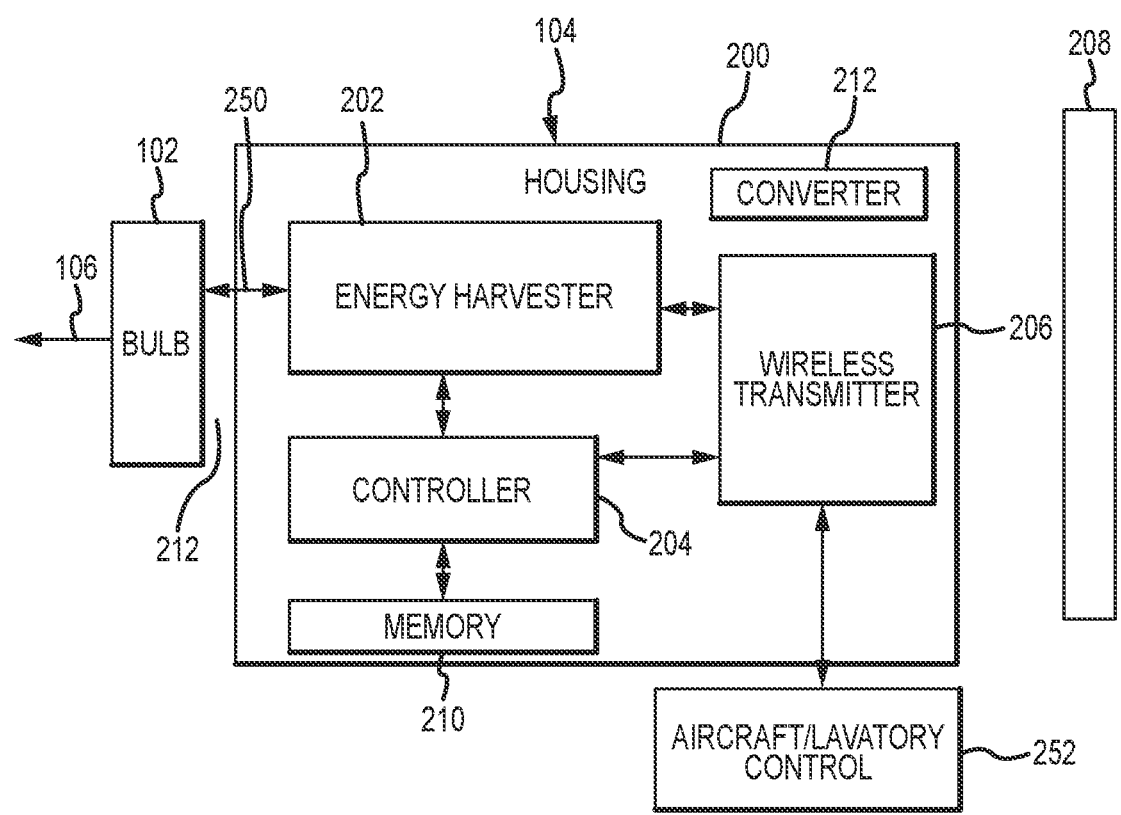

Turning now to FIGS. 2A and 2B, the monitoring device 104 may be located between the excimer bulb 102 and a heat sink 208 designed to collect and distribute thermal energy from the excimer bulb 102. Excimer bulbs 102 emit a relatively large amount of thermal energy (i.e., heat) compared to other ultraviolet light sources. However, excimer bulbs are currently the only light sources capable of emitting light of certain wavelengths (e.g., 222 nm).

Due to inclusion of the excimer bulb 102 and monitoring device 104 on board aircraft, it is desirable for the monitoring device 104 to use relatively little power. In that regard, the monitoring device 104 includes a thermoelectric energy harvester 202. The thermoelectric energy harvester 202 is designed to receive a portion of the thermal energy that is output by the excimer bulb 102 (hence the thermoelectric energy harvester 202 being located between the excimer bulb 102 and the heat sink 208) and to convert the received thermal energy into electrical energy.

The monitoring device 104 may further include a controller 204 and a wireless transmitter 206. The controller 204 may include one or more logic devices such as one or more of a central processing unit (CPU), an accelerated processing unit (APU), a digital signal processor (DSP), a field programmable gate array (FPGA), an application specific integrated circuit (ASIC), or the like. In various embodiments, the controller 204 may further include any non-transitory memory 210 known in the art. The memory 210 may store instructions usable by the logic device to perform operations. The memory 210 may also or instead store other data as instructed by the controller 204 such as historical remaining life values or historical temperatures of the excimer bulb 102.

The wireless transmitter 206 may at least one of transmit or receive wireless signals. For example, the wireless transmitter 206 may wirelessly communicate via a wireless protocol such as an 802.11a/b/g/n/ac protocol (e.g., Wi-Fi), a wireless communications protocol using short wavelength UHF radio waves and defined at least in part by IEEE 802.15.1 (e.g., the BLUETOOTH protocol maintained by Bluetooth Special Interest Group), a wireless communications protocol defined at least in part by IEEE 802.15.4 (e.g., the ZigBee protocol maintained by the ZigBee alliance), a cellular protocol, an infrared protocol, an optical protocol, a radio frequency identification (RFID) protocol, a near field communications (NFC) protocol, or any other protocol capable of wireless transmissions.

The monitoring device 104 may include a housing 200. The housing 200 may include a physical structure onto which the other components (i.e., one or more of the energy harvester 202, the controller 204, the memory 210, or the wireless transmitter 206) of the monitoring device 104 are affixed. In various embodiments, the other components may be at least one of surrounded by structure of the housing 200 or mounted on the housing 200 and at least partially exposed to the environment.

The monitoring device 104 may include a connector 212. The connector 212 may be coupled to the housing 200 and may affix the housing 200 to a portion of the excimer bulb 102 (or to a housing or other retaining structure of the excimer bulb 102). For example, the connector 212 may include a snap connector, a strap, a press-fit connector, or any other connector capable of affixing the housing 200 to the excimer bulb 102. The connector 212 may be designed such that the energy harvester 202 is located adjacent to the excimer bulb 102 at a constant, known distance 250. The distance 250 may be any distance sufficiently small for the energy harvester 202 to receive thermal energy from the excimer bulb 102. For example, the distance 250 may be between 0.1 inches (2.54 millimeters, mm) and 10 inches (254 mm), between 0.5 inches (12.7 mm) and 5 inches (127 mm), or between 1 inch (25.4 mm) and 2 inches (50.8 mm). The distance 250 may remain constant regardless of the excimer bulb 102 to which the housing 200 is affixed.

In response to being affixed to the excimer bulb 102, the energy harvester 202 may be directly exposed to the excimer bulb 102 such that no structure exists therebetween (i.e., thermal energy from the excimer bulb 102 may travel directly to the energy harvester 202). The energy harvester 202 may be placed on an opposite side of the excimer bulb 102 from which the ultraviolet light is desired (i.e., the energy harvester 202 may be located on an opposite side of the excimer bulb 102 from the direction indicated by the arrow 106) such that the housing 200 and energy harvester 202 fail to interfere with desirable operation of the ultraviolet light.

In response to receiving the thermal energy from the excimer bulb 102, the energy harvester 202 may generate electrical energy having a voltage. The voltage of the energy generated by the energy harvester 202 may be directly related to the temperature of the thermal energy received by the energy harvester 202. In that regard, the voltage may directly correspond to the temperature of the thermal energy. The controller 204 may receive the electrical energy from the energy harvester 202 and may determine at least one of the current temperature of the excimer bulb 102 or a remaining useful life of the excimer bulb 102 based on the voltage of the received electrical energy. In various embodiments, the controller 204 may calculate the current temperature and the remaining useful life.

In various embodiments, the memory 210 may store data received or determined by the controller 204. For example, the memory 210 may store historical data such as historical voltages of the electrical energy received by the controller 204, historical calculated temperatures of the excimer bulb 102, or historical remaining useful life of the excimer bulb 102. In that regard, the controller 204 may calculate at least one of the remaining useful life of the excimer bulb 102 or the current temperature of the excimer bulb 102 based on this historical data. For example, the controller 204 may compare a current calculated temperature of the excimer bulb 102 to a historical calculated temperature of the excimer bulb 102 to determine a remaining useful life of the excimer bulb 102. As another example, the controller 204 may compare a current received voltage to a historically received voltage to determine the remaining useful life of the excimer bulb 102. In various embodiments, the controller 204 may calculate a remaining useful life of the excimer bulb 102 as a remaining quantity of hours of useful life of the excimer bulb 102. In various embodiments, the controller 204 may calculate a remaining useful life of the excimer bulb 102 based on additional data such as a voltage waveform provided to the excimer bulb 102, a current waveform provided to the excimer bulb 102, or the like.

The controller 204 may be in electrical communication with the wireless transmitter 206. In that regard, the wireless transmitter 206 may transmit data received or calculated by the controller 204. The wireless transmitter 206 may be capable of transmitting signals to be received by an aircraft controller 252 (which may include a controller responsible for monitoring the status of components of the lavatory 100 of FIG. 1). For example, the wireless transmitter 206 may transmit the current calculated temperature and the remaining useful life of the excimer bulb 102 to the aircraft controller 252. In various embodiments, the wireless transmitter 206 may also or instead transmit lower-level data such as the detected voltage of the electrical power generated by the energy harvester 202.

As referenced above, it is desirable for the monitoring device 104 to draw relatively little power from the aircraft. In that regard, the electrical energy generated by the energy harvester 202 may be transmitted to the controller 204, the memory 210, and the wireless transmitter 206 and may be used to power the controller 204, the memory 210, and the wireless transmitter 206. In some embodiments, the monitoring device 104 may also include one or more energy converter 212 capable of converting or otherwise formatting the electrical power generated by the energy harvester 202 into electrical power having a voltage, amplitude, and frequency (in the case of alternating current) that is usable by each of the controller 204, the memory 210, and the wireless transmitter 206. In that regard, the monitoring device 104 is self-contained and self-powering such that the only wires used in relation to the excimer bulb 102 are the wires that provide power to the excimer bulb 102. This reduces the complexity of the lavatory 100 of FIG. 1 as well as the power draw by the system.

Figure 3:
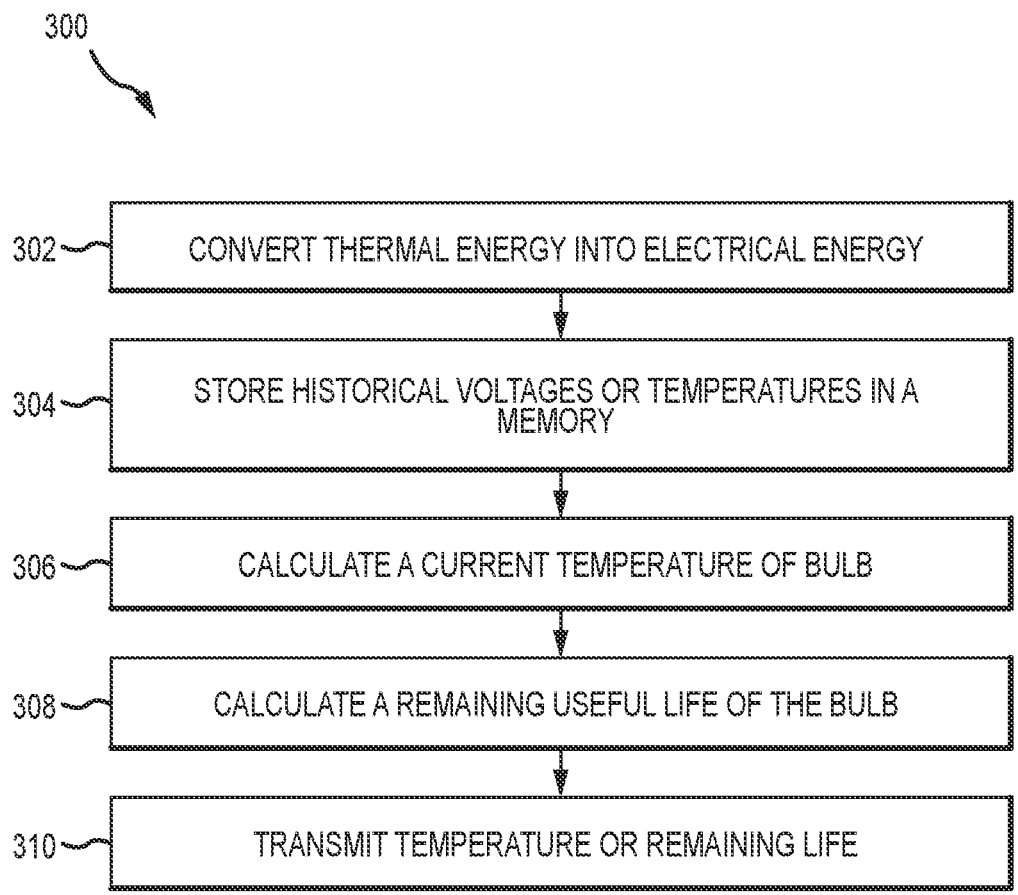
FIG. 3 is a flowchart illustrating a method for monitoring a status of an excimer ultraviolet bulb, in accordance with various embodiments.

Turning now to FIG. 3, a flowchart illustrates a method 300 for monitoring an excimer bulb. The method 300 may be used by a monitoring device similar to the monitoring device 104 of FIGS. 2A and 2B, and may monitor an excimer bulb such as the excimer bulb 102 used in the aircraft lavatory 100 of FIG. 1. The method 300 may begin in block 302 where a thermoelectric energy harvester receives thermal energy from an excimer bulb and converts the thermal energy into electrical energy having a voltage.

In block 304, a memory may store historical data such as historical voltages of the electrical energy output by the harvester, historically calculated temperatures of the excimer bulb, or historically calculated remaining useful life of the excimer bulb.

In block 306, a controller may receive the electrical power from the harvester and may also receive historical data from the memory. The controller may then calculate a current temperature of the excimer bulb based on at least one of the current voltage of the electrical power from the harvester or the historical data from the memory.

In block 308, the controller may calculate a remaining useful life of the excimer bulb. For example, the controller may calculate the remaining useful life based on the current voltage of the electrical power and based on the historical data.

In block 310, a wireless transmitter may transmit at least one of the current temperature or the remaining useful life of the excimer bulb to an aircraft controller. As with the monitoring device 104 shown in FIGS. 2A and 2B, the controller, memory, and wireless transmitter discussed with reference to FIG. 3 may be entirely powered using the electrical energy output by the thermoelectric energy harvester.

Benefits and other advantages have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, and any elements that may cause any benefit or advantage to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

Systems, methods and apparatus are provided herein. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 12(f), unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A system for monitoring an excimer bulb, the system comprising:
   a thermoelectric energy harvester configured to be located adjacent to the excimer bulb and to convert thermal energy from the excimer bulb into electrical energy having a voltage; and
   a controller in electrical communication with the thermoelectric energy harvester and configured to calculate at least one of a remaining useful life of the excimer bulb or a current temperature of the excimer bulb based on the voltage of the electrical energy converted by the thermoelectric energy harvester.

2. The system of claim 1, wherein the controller is further configured to calculate the remaining useful life of the excimer bulb based on at least one of the current temperature of the excimer bulb, a previously-calculated historical temperature of the excimer bulb, the current voltage of the electrical energy converted by the thermoelectric energy harvester, or a previous voltage of the electrical energy converted by the thermoelectric energy harvester.

3. The system of claim 2, further comprising a memory configured to store historical data corresponding to at least one the previously-calculated historical temperature of the excimer bulb or the previous voltage of the electrical energy converted by the thermoelectric energy harvester, and the controller is further configured to calculate the remaining useful life of the excimer bulb by comparing at least one of the current temperature of the excimer bulb or the current voltage of the electrical energy converted by the thermoelectric energy harvester to the historical data.

4. The system of claim 1, further comprising a wireless transmitter coupled to the controller and configured to transmit the at least one of the remaining useful life of the excimer bulb or the current temperature of the excimer bulb to a remote device.

5. The system of claim 4, wherein the wireless transmitter is configured to be powered using the electrical energy generated by the thermoelectric energy harvester.

6. The system of claim 4, further comprising a housing configured to house the thermoelectric energy harvester, the controller, and the wireless transmitter.

7. The system of claim 1, wherein the controller is configured to be powered using the electrical energy generated by the thermoelectric energy harvester.

8. The system of claim 1, wherein the excimer bulb emits ultraviolet light for damaging or destroying pathogens, and the system is configured for use in an aircraft.

9. The system of claim 1, wherein the controller is configured to calculate both of the remaining useful life of the excimer bulb and the current temperature of the excimer bulb.

10. The system of claim 1, wherein the controller is configured to calculate the remaining useful life of the excimer bulb as hours of useful life remaining.

11. A system for monitoring an excimer bulb, the system comprising:
   a thermoelectric energy harvester configured to be located adjacent to the excimer bulb and to convert heat from the excimer bulb into electrical energy having a voltage; and
   a controller in electrical communication with the thermoelectric energy harvester and configured to:
      calculate a current temperature of the excimer bulb based on the voltage of the electrical energy converted by the thermoelectric energy harvester, and
      calculate a remaining useful life of the excimer bulb based on at least one of the voltage of the electrical energy converted by the thermoelectric energy harvester or the current temperature of the excimer bulb.

12. The system of claim 11, further comprising a wireless transmitter coupled to the controller and configured to transmit at least one of the remaining useful life of the excimer bulb or the current temperature of the excimer bulb to a remote device.

13. A method for monitoring an excimer bulb, the method comprising:
   converting, by a thermoelectric energy harvester, thermal energy received from an adjacent excimer bulb into electrical energy having a voltage; and
   calculating, by a controller, at least one of a remaining useful life of the excimer bulb or a current temperature of the excimer bulb based on the voltage of the electrical energy converted by the thermoelectric energy harvester.

14. The method of claim 13, wherein calculating the remaining useful life of the excimer bulb is performed based on at least one of the current temperature of the excimer bulb, a previously-calculated historical temperature of the excimer bulb, the current voltage of the electrical energy converted by the thermoelectric energy harvester, or a previous voltage of the electrical energy converted by the thermoelectric energy harvester.

15. The method of claim 14, further comprising storing, in a memory, historical data corresponding to at least one the previously-calculated historical temperature of the excimer bulb or the previous voltage of the electrical energy converted by the thermoelectric energy harvester, wherein calculating the remaining useful life of the excimer bulb is performed by comparing at least one of the current temperature of the excimer bulb or the current voltage of the electrical energy converted by the thermoelectric energy harvester to the historical data.

16. The method of claim 13, further comprising transmitting, by a wireless transmitter, the at least one of the remaining useful life of the excimer bulb or the current temperature of the excimer bulb to a remote device.

17. The method of claim 16, wherein the wireless transmitter is powered using the electrical energy generated by the thermoelectric energy harvester.

18. The method of claim 13, wherein the controller is powered using the electrical energy generated by the thermoelectric energy harvester.

19. The method of claim 13, wherein calculating the at least one of the remaining useful life of the excimer bulb or the current temperature of the excimer bulb includes calculating both of the remaining useful life of the excimer bulb and the current temperature of the excimer bulb.

20. The method of claim 13, wherein calculating the remaining useful life of the excimer bulb includes calculating a number of hours of remaining useful life remaining.

* * * * *